United States Patent [19]

Eppolito

[11] 4,383,528

[45] May 17, 1983

[54] OXYGEN CADDY

[76] Inventor: Salvatore Eppolito, 77 Wert Ave., Trenton, N.J. 08610

[21] Appl. No.: 255,565

[22] Filed: Apr. 20, 1981

[51] Int. Cl.[3] .............................................. A61M 16/00

[52] U.S. Cl. .......................... 128/205.22; 128/204.18; 224/225; 224/227; 224/210; 224/259

[58] Field of Search ........................ 128/201.27, 201.29, 128/205.22, 202.13, 204.18, 200.24; 224/201, 204, 205, 225, 227, 908, 209, 210, 211, 212, 259; 229/214

[56] References Cited

U.S. PATENT DOCUMENTS

| | | | |
|---|---|---|---|
| 2,836,334 | 5/1958 | Davis | 224/210 |
| 4,074,839 | 2/1978 | Wood et al. | 224/212 |
| 4,169,550 | 10/1979 | Williams | 224/211 |

FOREIGN PATENT DOCUMENTS

| | | | |
|---|---|---|---|
| 199348 | 11/1938 | Switzerland | 224/210 |

OTHER PUBLICATIONS

Robertshaw Controls Company Medical Products Catalog.

*Primary Examiner*—Henry J. Recla
*Attorney, Agent, or Firm*—Sanford J. Asman

[57] ABSTRACT

The oxygen caddy is a carrier for an oxygen tank of the type used by emergency medical personnel. It includes a fabric case which covers a rigid, protective, supporting frame in which the oxygen tank is held. The case includes pockets in which oxygen delivery means, such as a demand valve, an inhalator, or an aspirator, may be stored for use. The oxygen delivery means, such as a demand valve, an inhalator, or an aspirator, are attached to the oxygen tank via hoses which extend into the pockets through openings in the case. A shoulder strap is provided in order to allow emergency personnel to carry the oxygen carrier without using his hand, which is then free to carry other equipment.

8 Claims, 9 Drawing Figures

OXYGEN CADDY

BACKGROUND OF THE INVENTION

The present invention relates to a carrier unit, or caddy, for a bottled gas, such as oxygen. In particular, the invention relates to a carrier, called "OXY-CADDY" by its inventor, for portable oxygen tanks and resuscitators of the type used by first aid and emergency squads.

Oxygen contained in metal bottles has long been used for medical purposes. Such bottled oxygen is generally taken to the location of the victim of a medical emergency, such as a choking victim or a heart attack victim.

Heretofore, oxygen bottles, or tanks, of the type with which the present invention is used, were carried in various types of rigid carriers. The reason for using rigid carriers has been to afford protection to the cutoff valve which must be installed on the tank in order to deliver oxygen as it is needed. Such carriers have generally been constructed of wood or metal, and as such, they have been relatively heavy and unwieldy.

Some newer carriers are constructed of plastic, in order to cut down on their weight and to provide a carrying handle which allows the oxygen tank to be carried more easily by emergency personnel. However, various problems have been encountered with the plastic carriers. In particular, they require that the emergency personnel devote a hand to hold the oxygen carrier, which prevents them from carrying something else in that hand. In addition, the plastic carriers have not generally held up well in use.

Generally, emergency personnel carry a lot of equipment in addition to oxygen tanks on their ambulances and emergency vehicles. Due to the increased amount of such equipment, which includes cardiac telemetry equipment and drug kits, among many other items, it is desirable to provide an oxygen carrier which can be carried by such personnel, yet which still leaves their hands free to carry other items. In addition, an oxygen carrier which protects the valve or regulator at the top of the oxygen tank is desirable.

Finally, multipurpose regulators are now available which provide for the attachment of multiple oxygen delivery means, including demand valves, aspirators, and inhalators. By way of example, a three-way valve of the type described is presently available from Robertshaw Controls Company, Life Support Products Marketing Group, 333 N. Euclid Way, Anaheim, California 92803.

It would be highly desirable to have an oxygen tank carrier which could be carried by emergency personnel which would make each of the aforementioned oxygen delivery means available for instant use and which allowed the emergency personnel to utilize their hands to carry other equipment onto the scene of the emergency.

SUMMARY OF THE INVENTION

In accordance with the present invention an oxygen carrier or caddy is provided which is comprised of a rigid frame designed to surround and protect the oxygen bottle and its valve. The frame is covered by a case made of a durable material, such as canvas. The case preferably contains pockets in which the various oxygen delivery means are normally stored. In addition, the oxygen caddy preferably has a shoulder strap which can be slung over the shoulder of the emergency personnel carrying the oxygen in order to leave his hands free for other purposes. Openings in the covering material allow appropriate hoses from the valve to pass directly from the valve into the pockets whereby the oxygen bottle, valve, regulator, and delivery means are fully protected when stored, but are instantly available for use when necessary.

DETAILED DESCRIPTION OF AN EXEMPLARY EMBODIMENT

Figure 1:
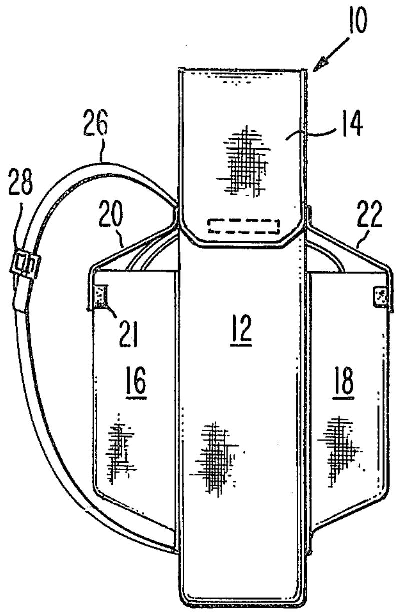
FIG. 1 is a front view of the oxygen caddy of the preferred embodiment of the invention showing the oxygen caddy as it is normally stored.
Figure 2:
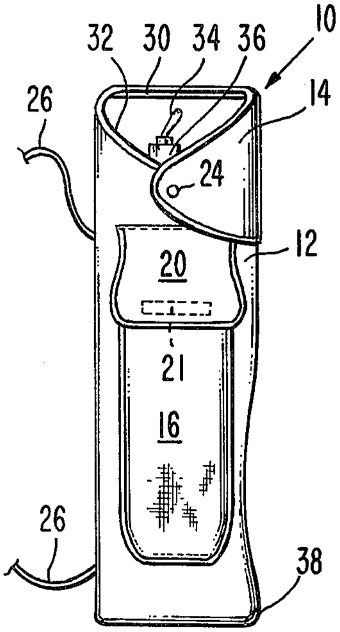
FIG. 2 is a side view of the oxygen caddy of FIG. 1.

Referring generally to FIGS. 1–4, the oxygen caddy 10 of the preferred embodiment of the present invention is shown. The oxygen caddy 10 comprises a case 12 made of a durable covering material, typically a fabric such as canvas or nylon. The case 12 has a top flap 14 which closes over the top of an oxygen tank (not shown). On either side of the case 12, there are pockets 16, 18, which have flaps 20, 22, respectively. The purpose of the pockets 16, 18 is to carry oxygen delivery means, as will be seen hereinafter. In the preferred embodiment of the invention, hook and loop fasteners, such as Velcro fasteners are used to close the flaps 20, 22 on the side pockets 16, 18, thereby allowing them to be readily opened to expose the oxygen delivery means contained in them as will be seen more fully hereinafter. The top flap 14, is preferably closed using a hook and loop fastener across its front and snaps, such as snap 24, as shown in FIG. 2, on either side.

The oxygen caddy 10 further comprises a shoulder strap 26, which is attached to the back of the caddy 10 and which is preferrably made of a strong, flat material, such as canvas strapping. The shoulder strap 26 preferably includes an adjustment means, such as a buckle 28, which may be used to alter its length for the comfort and convenience of the particular individual who will be carrying the caddy 10. The caddy 10 may be carried either over one's shoulder by using the strap 26, or by hand, either by holding the strap 26, or by using the top of the frame 30 as a handle.

With particular reference to FIG. 2, the top of the case 12 is preferably designed to have an opening 32 which exposes the top of the frame 30 so that it may be used as a handle in the manner referred to. In addition, the opening 32 provides immediate access to a cutoff valve 34 which is attached to the top of an oxygen tank (not shown), in order to allow the emergency personnel to readily turn on the oxygen flow without opening the top flap 14, thereby decreasing the time required to administer oxygen to an individual in need thereof. It will be recognized by those skilled in the art that the type of cutoff valve 34 which is illustrated represents only one type of cutoff valve, and the use of this particular type of cutoff valve is not critical to the present invention.

With continued reference to FIG. 2, the bottom of the caddy 10 of the preferred embodiment of the invention includes a base portion 38 which is broader, when viewed from the side, than the remaining portions of the caddy 10. The purpose of the broadened base portion 38 is to stabilize the caddy 10 in order to prevent it from falling over when in use.

Figure 3:
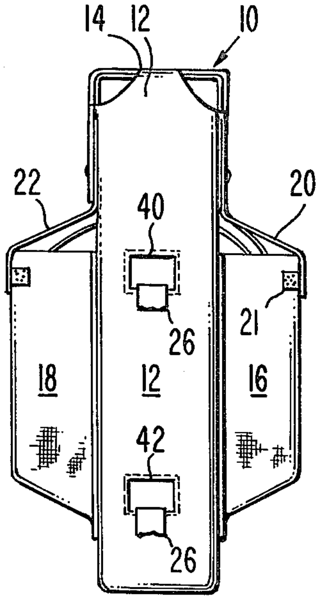
FIG. 3 is a rear view of the oxygen caddy of FIG. 1 with the shoulder strap removed.

Referring now also to FIG. 3, a rear view of the caddy 10, shows that in the preferred embodiment of the caddy 10 openings, 40, 42 are formed in the case 12 in order to allow the shoulder strap 26 to be attached to the caddy 10. The shoulder strap 26 could be sewn or otherwise attached directly to the covering material of the case 12. However, in the preferred embodiment of the invention, the frame 30 includes support members, as will be seen, and the shoulder strap 26 is comprised of a strap with a buckle 28, as shown in FIG. 1, and it is not directly attached to the caddy 10. Instead, the strap 26 is threaded into one of the openings 40 and out of the other opening 42. Then, the end of the strap 26 is buckled. Thus, if a shoulder strap 26 is damaged, it may be easily and readily replaced.

Figure 4:
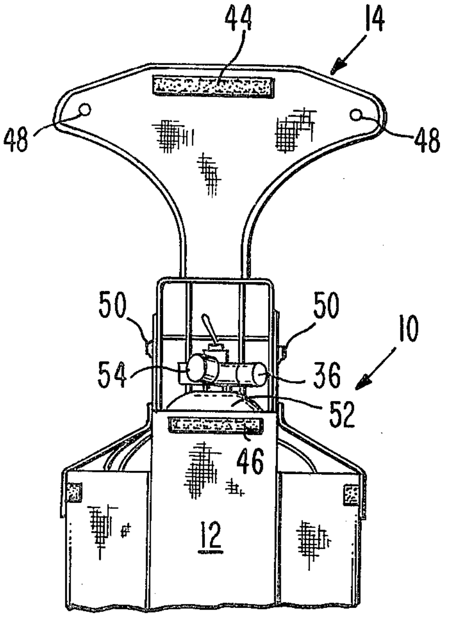
FIG. 4 is an exploded view of the top of the caddy of FIG. 1 with the top flap opened.

Referring now to FIG. 4, an exploded view of the front top portion of the caddy 10, with the top flap 14 open, is shown. One component 44 of the hook and loop fastener is attached to the inside of the flap 14, and the other component 46 of the hook and loop fastener is attached to the top of the case 12. Similarly, one component 48 of each snap 24 is attached to each side of the top flap 14 and the other component 50 of each snap 24 is attached to the either side of the case 12. With the top flap 14 opened, the top of the oxygen tank 52 and the pressure gauge 54 on the regulator 36 are exposed. Thus, the pressure gauge 54 may be readily observed in order to determine the quantity of oxygen remaining in the tank 52.

Figure 5:
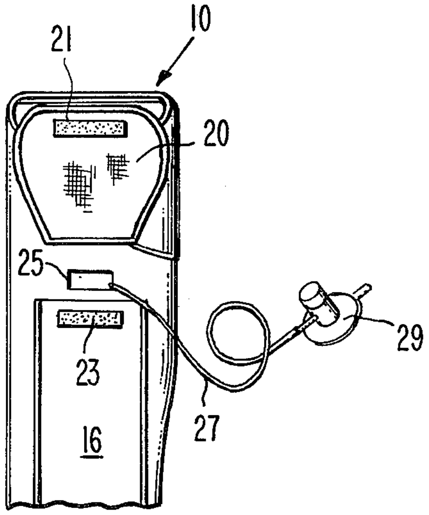
FIG. 5 is an exploded view of one side of the caddy of FIG. 1 with the side flap opened.

With particular reference to FIG. 5, with the wide flap 20 opened, the portions 21, 23 of the hook and loop fastener which keeps the flap 20 closed, are shown. Also, an opening 25 in the side of the case 12 can be seen with the flap 20 open. The purpose of the opening 25 is to allow a hose 27 to pass from the valve on the oxygen tank (not shown), through the case 12 to one of the oxygen delivery means 29 which is normally stored in the pocket 16. The particular oxygen delivery means 29 which is illustrated is a demand valve. However, any other delivery means, such as an aspirator or an inhalator, could also be attached to the hose 27. If a three-way valve, such as the one identified above, is used on the oxygen tank, then each of the three types of oxygen delivery means can be left attached so that any of them would be available for immediate use. In such case, one delivery means would be stored in one of the pockets 16, 18, and the other two delivery means would be stored in the other one of the pockets 18, 16.

Referring now to FIGS. 6–9, the frame 30 of the caddy 10 is shown with the case 12 removed. The frame 30 of the preferred embodiment of the invention is comprised of a series of welded rods which are arranged in a manner which protects an oxygen tank 52. However, the frame 30 could also be comprised of a formed material, such as metal or plastic which includes appropriate openings.

Figure 6:
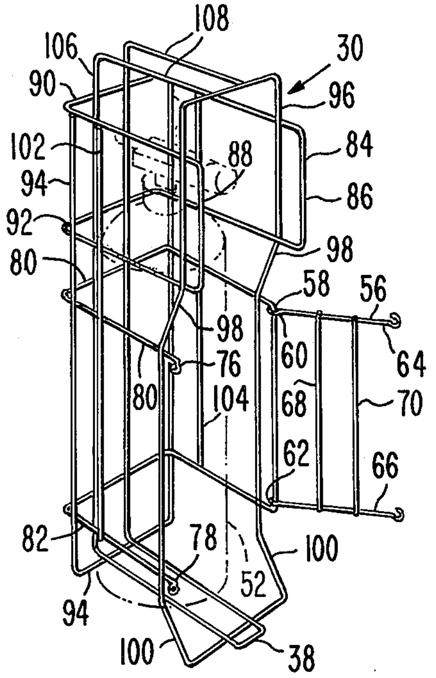
FIG. 6 is an illustration of a perspective view of the frame of the oxygen caddy of FIG. 1 with an oxygen tank shown in shadow.
Figure 7:
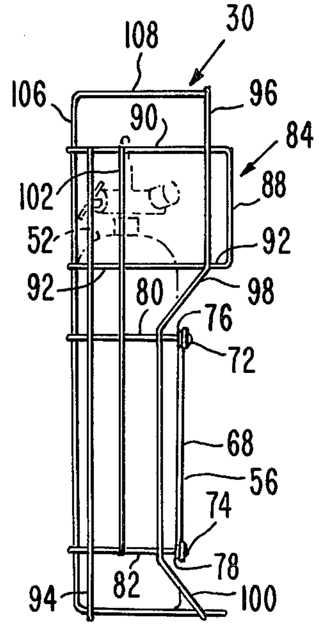
FIG. 7 is a side view of the frame of FIG. 6 holding an oxygen tank.
Figure 8:
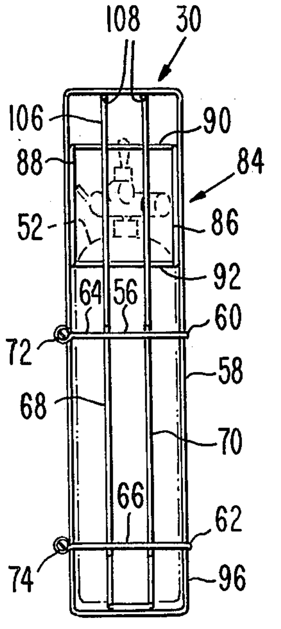
FIG. 8 is a front view of the frame of FIG. 6 holding an oxygen tank.
Figure 9:
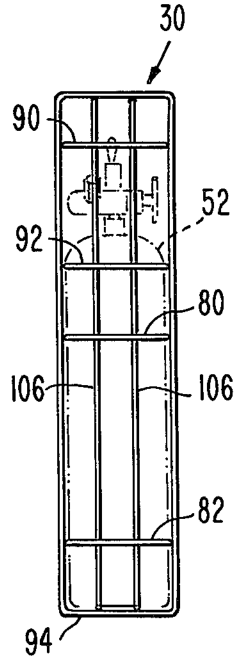
FIG. 9 is a rear view of the frame of FIG. 6 holding an oxygen tank.

The frame 30 includes a door 56 which is attached to a vertical front member 58 by hinges 60, 62. In the preferred embodiment of the frame 30, the door 56 is comprised of upper and lower rods 64, 66 which are spaced from one another and connected together to form a door by vertical door members 68, 70. The hinges 60, 62 are comprised of portions of the upper and lower members 64, 66 which are formed around the vertical front member 58. Accordingly, the hinges 60, 62 have no moving parts, yet they allow the door 56 to be opened, as shown in FIG. 6, so that the oxygen tank 52 may be inserted into the frame 30. In its closed position, the door 56 secures the tank 52 in position. The door 56 is held in its closed position by bolts 72, 74 (shown in FIGS. 7 and 8) which are screwed into threaded portions 76, 78 welded to upper and lower horizontal support members 80, 82. In the preferred embodiment of the invention, the horizontal support members 80, 82 are made of a single rod which extends from upper member 80, around the back and other side of the frame 30 to the top of vertical front member 58. Similarly, the lower horizontal support member 82 extends around the side and back of the frame 30 to the bottom of vertical member 58.

A regulator protecting cage 84 is formed in a similar manner with vertical portions 86, 88 and upper and lower horizontal portions 90, 92 made of a single, formed rod. The upper and lower horizontal portions 90, 92 are U-shaped to extend around the sides and back of the frame 30, and the ends of the rod are welded together, forming a continuous loop.

The frame 30 further comprises a U-shaped rear support member 94 which extends vertically on either side of the frame 30, with its bottom forming part of the bottom of the frame 30. A front support member 96 is a formed, closed loop having angular upper and lower portions 98, 100. The upper angular portions 98 are required in order to allow room within the upper portion of the frame 30 for the regulator protecting cage 84, which is wider than the diameter of the tank 52. The lower angular portions 100 are required to provide the wide base 38 on the bottom of the frame 30.

A pair of vertical supports 102, 104 are welded to the sides of the frame 30 in order to provide extra longitudinal support. The vertical supports 102, 104 extend from the upper horizontal portion 90 of the regulator protecting cage 84 to the lower horizontal support member 82.

Finally, a formed U-shaped rod 106, forms a handle 108 at the top of the frame 30, extends vertically down the rear of the frame 30, then extends along the bottom of the frame 30 to form its base 38. The components of the frame 30 are welded together at the points where the members cross each other, thereby providing a strong, protective cage which holds the oxygen tank 52.

After the oxygen tank 52 is inserted into the frame 30, the frame 30 is inserted into the case 12. The horizontal member 92 and the horizontal member 82 are at heights which are just below the opening 40 and just above the opening 42, respectively, in the rear of the case 12. Thus, when the shoulder strap 26 is inserted through the openings 40, 42, it is threaded through the frame 30 to enclose the horizontal members 80, 82, and 90 in order to support the frame 30 directly.

As will be understood by those of ordinary skill in the art, the important features of the frame 30 are that it protects the tank 52 by enclosing it. Yet, it allows the tank 52 to be easily and readily inserted and removed. In addition, it provides an upper carrying handle 108 and a broad lower base 38. Also, it has provision to connect the shoulder strap 26 securely to it. Finally, with all of these features, it remains light in weight. While these features are important aspects and features of the invention, various ones of them, or all of them, may be obtained by using a formed, solid frame, rather than the welded frame 30 of the preferred embodiment.

I claim:

1. An oxygen caddy which comprises:

(a) a rigid supporting frame adapted to hold and completely surround an oxygen tank together with its regulator and valve;

(b) a fabric case which surrounds said rigid supporting frame, said case including at least two pockets in which oxygen delivery means may be stored, and an opening extending through said case into each of said pockets, whereby a hose connecting an oxygen delivery means may extend through said case and into each of said pockets.

2. The oxygen caddy of claim 1 further comprising a shoulder strap attached to said case, whereby said oxygen caddy can be carried by said shoulder strap.

3. The oxygen caddy of claim 2 wherein the shoulder strap includes means for adjusting its length.

4. The oxygen caddy of claim 1 in which said rigid supporting frame is comprised of metal rods welded together to form a protective cage around an oxygen bottle carried in said oxygen caddy.

5. The oxygen caddy of claim 4 wherein the top of said frame is adapted for use as a handle.

6. The oxygen caddy of claim 5 wherein said case is comprised of canvas.

7. The oxygen caddy of claim 5 wherein said case is comprised of nylon.

8. The oxygen caddy of claim 4 wherein the bottom of said frame is formed into a wide, stable base.

* * * * *